US00PP26122P3

(12) United States Plant Patent
Conev et al.

(10) Patent No.: US PP26,122 P3
(45) Date of Patent: Nov. 24, 2015

(54) DWARF GRAPEVINE 'VDG001'

(50) Latin Name: *Vitis vinifera*
Varietal Denomination: VDG001

(71) Applicant: Vineland Research and Innovations Centre Inc., Vineland Station (CA)

(72) Inventors: Rumen Conev, St. Catharines (CA); Daryl Somers, Fenwick (CA)

(73) Assignee: Vineland Research and Innovations Centre Inc., Vineland Station (CA)

( * ) Notice: Subject to any disclaimer, the term of this patent is extended or adjusted under 35 U.S.C. 154(b) by 64 days.

(21) Appl. No.: 13/999,596

(22) Filed: Mar. 12, 2014

(65) Prior Publication Data

US 2014/0359904 P1 Dec. 4, 2014

(30) Foreign Application Priority Data

Jun. 6, 2013 (CA) ..... 13-8052

(51) Int. Cl.
*A01H 5/00* (2006.01)
*A01H 5/08* (2006.01)

(52) U.S. Cl.
USPC ..... Plt./207
CPC ..... *A01H 5/0812* (2013.01)

(58) Field of Classification Search
USPC ..... Plt./207
See application file for complete search history.

(56) References Cited

PUBLICATIONS

PLUTO Plant Variety Database Jul. 9, 2015.*

* cited by examiner

*Primary Examiner* — Annette Para

(57) ABSTRACT

The invention is a new and distinct ornamental dwarf grapevine variety denominated 'VDG001'. The new grapevine is characterized by light to medium green leaf color, reddish petiole, smooth mature leaf surface, petiole sinus with closed lobes, circular mature leaf, some veins with anthocyanin coloration and green berries.

5 Drawing Sheets

Latin name of the genus and species of the plant claimed: *Vitis vinifera.*

Variety denomination: 'VDG001'.

BACKGROUND OF THE INVENTION

The new and distinct dwarf ornamental grapevine described and claimed herein originated from a cross between 'Pixie'™×'Riesling'.

The female parent 'Pixie'™ is a natural dwarf ornamental grapevine (*Vitis vinifera*) derived from periclinal L1/L2 chimera 'Pinot Meunier' with dark purple berry skin. 'Pixie'™ is the only known naturally dwarf grapevine in the public domain.

The pollen parent 'Riesling' is an early 15$^{th}$ century *Vitis vinifera* variety from Germany.

The present variety of dwarf grapevine was first produced by controlled hybridization. The original cross was done at Vineland Research and Innovations Centre, Vineland Station, Ontario, Canada on Oct. 20, 2010.

'VDG001' was first successfully asexually propagated by single node softwood cuttings at the Vineland Research and Innovations Centre, Vineland Station, Ontario, Canada on Jun. 8, 2012. It is being maintained on its own roots in a container in a Canadian Food Inspection Agency certified greenhouse facility at Vineland Research and Innovation Centre, Vineland Station, Ontario, Canada.

SUMMARY OF THE INVENTION

The new grapevine 'VDG001' has the following major distinguishing characteristics. Mature leaf in 'VDG001' is smaller than in 'Pixie'™. Leaf color in 'VDG001' is light to medium green, whereas mature leaf is dark green in 'Pixie'™. Petiole in 'VDG001' is reddish, whereas petiole is green in 'Pixie'™. Mature leaf surface in 'VDG001' is smooth, whereas mature leaf surface has a prominent blistery texture in 'Pixie'™. Petiole sinus in 'VDG001' has closed lobes, whereas petiole sinus has half overlapping lobes in 'Pixie'™. Mature leaf in 'VDG001' has circular shape, whereas mature leaf has a pentagonal shape in 'Pixie'™. 'VDG001' has some veins with anthocyanin coloration, whereas in 'Pixie'™ all veins are green.

The characteristics most useful in distinguishing 'VDG001' from 'Pixie'™ are young shoot: anthocyanin coloration of prostrate hairs on tip, young leaf: prostrate hairs between main veins on lower side of blade, mature leaf: blistering of upper side of blade, mature leaf: depth of upper lateral sinuses, mature leaf: erect hairs on main veins on lower side of blade, bunch: length of peduncle of primary bunch, and berry: color of skin (without bloom).

BRIEF DESCRIPTION OF THE DRAWING

The accompanying photographic illustration illustrates in full color 'VDG001'. The colors are as nearly true as reasonably possible in color representation of this type. Colors in the photographs may differ from the color values cited in the detailed botanical description below, which accurately describes the colors of the new dwarf grapevine.

DETAILED BOTANICAL DESCRIPTION OF THE INVENTION

Figure 1:
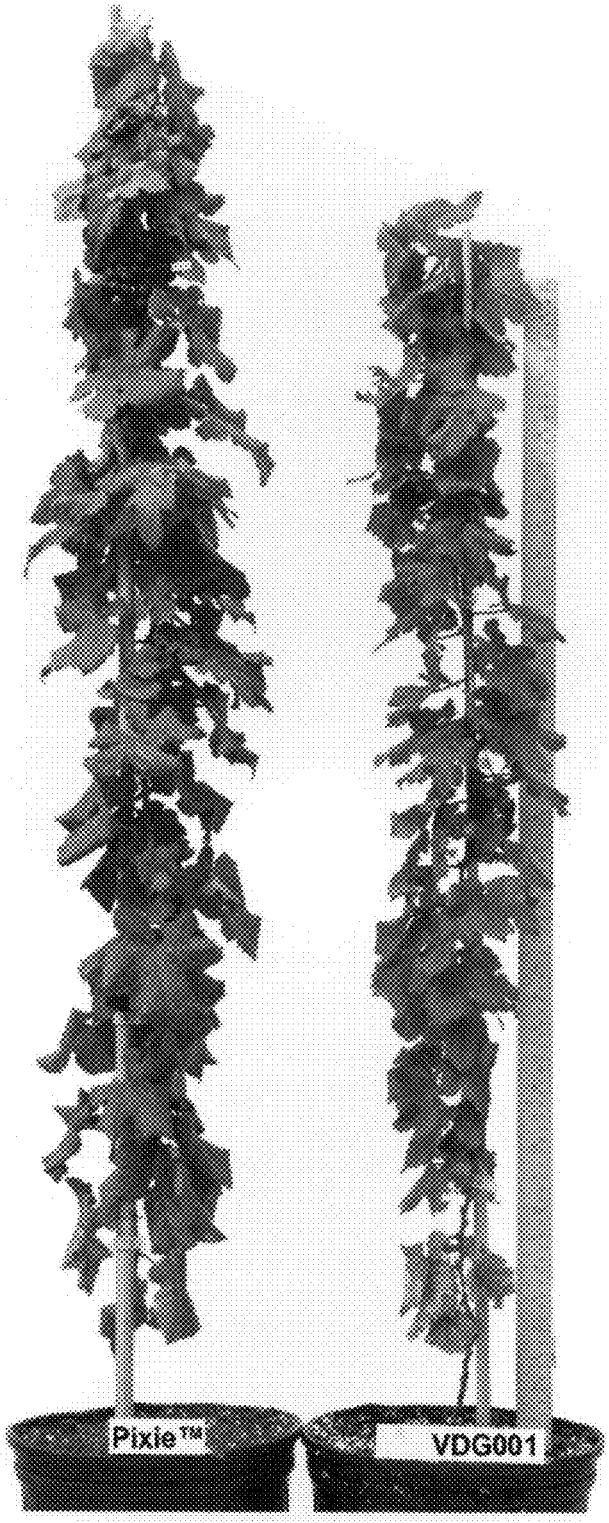
FIG. 1 shows habit and foliage color of 'VDG001', in comparison to the female parent 'Pixie'™.
Figure 2:
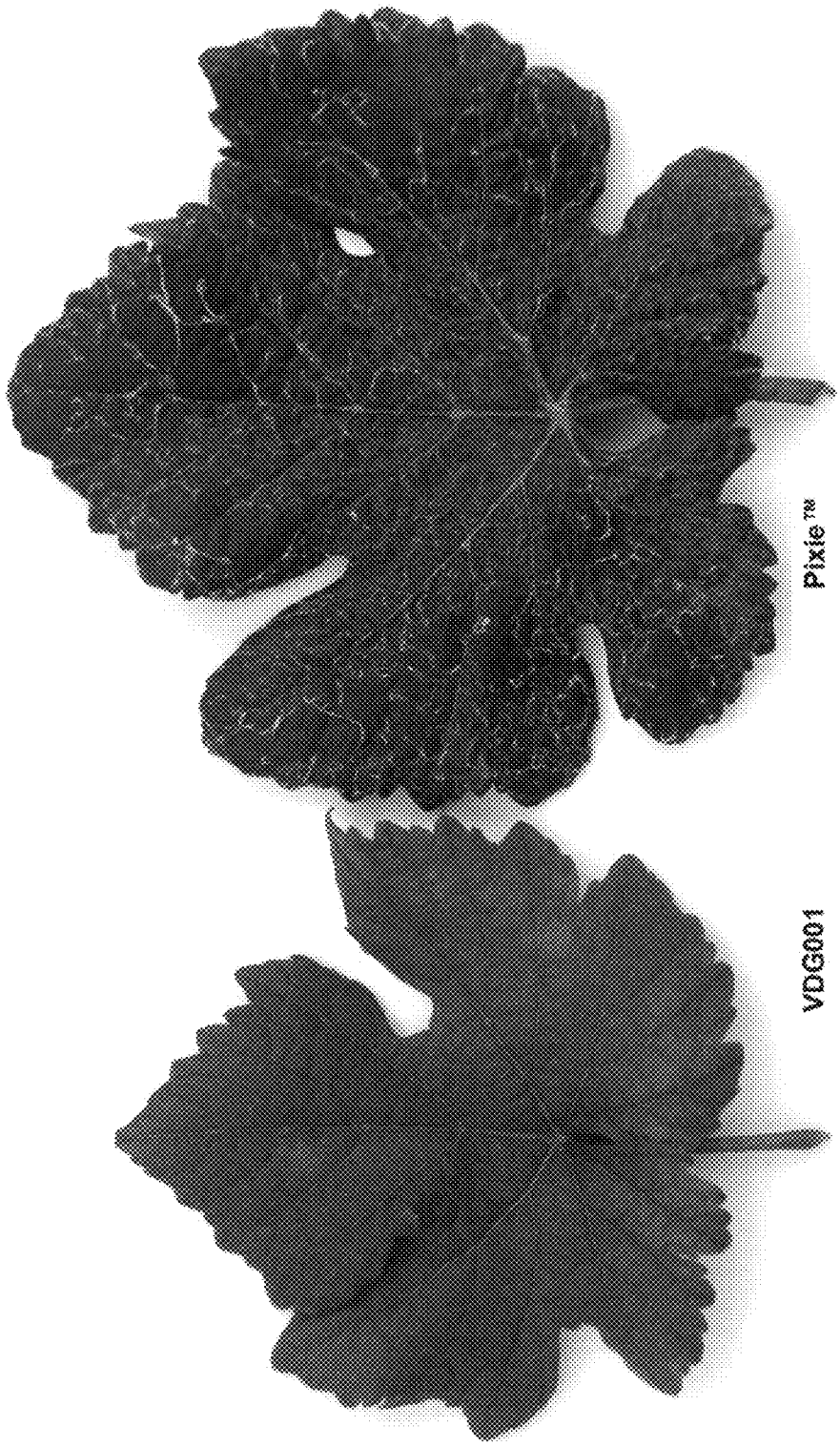
FIG. 2 shows upper side of mature leaf blade of 'VDG001', in comparison to the female parent 'Pixie'™.
Figure 3:
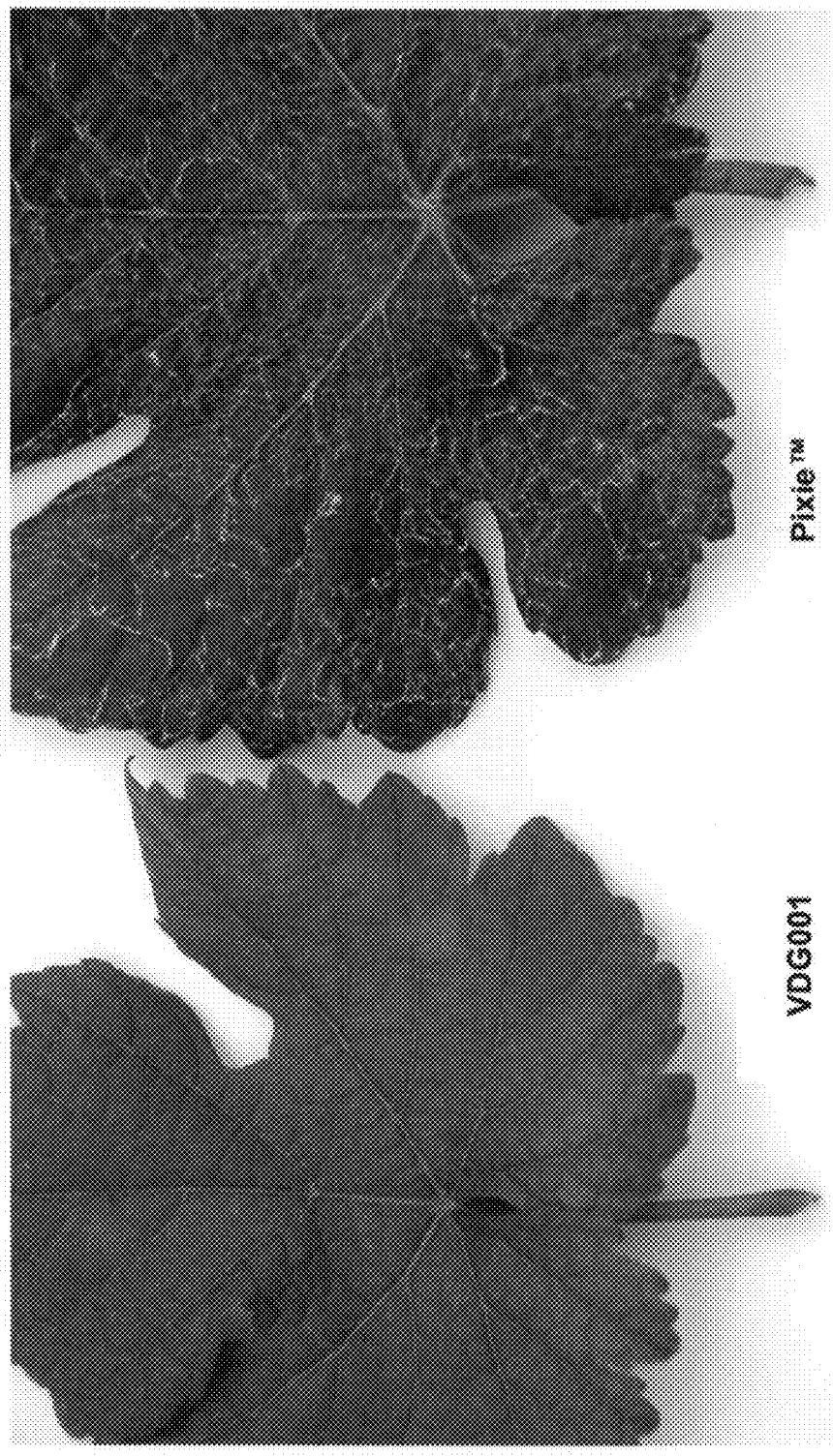
FIG. 3 shows a magnified view of upper side of mature leaf blade of 'VDG001', in comparison to the female parent 'Pixie'™.
Figure 4:
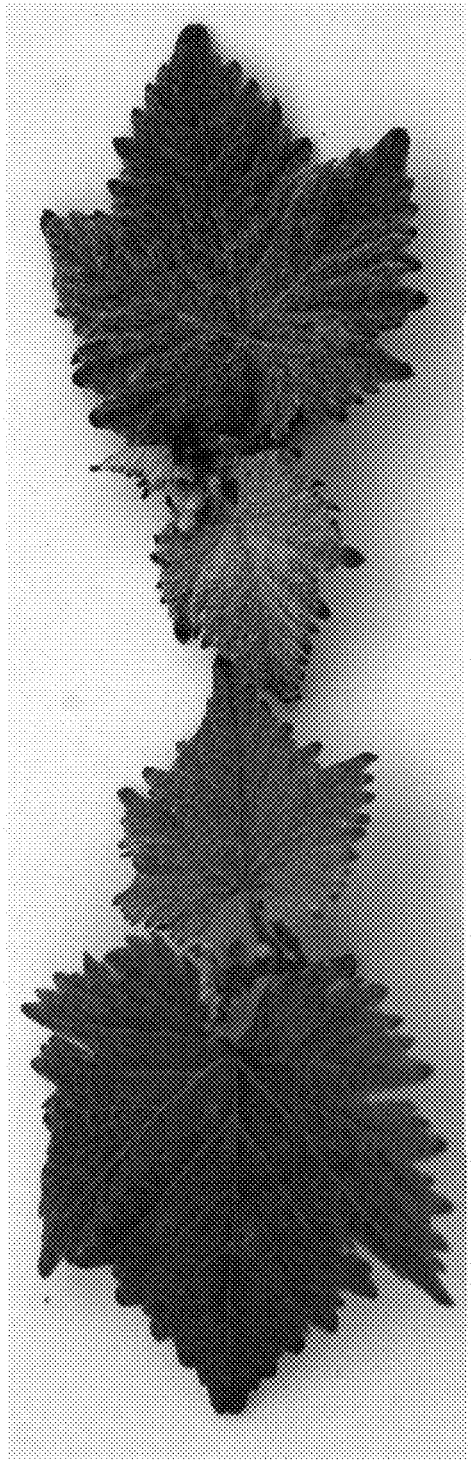
FIG. 4 shows upper side of young shoot of 'VDG001', in comparison to the female parent 'Pixie'™.
Figure 5:
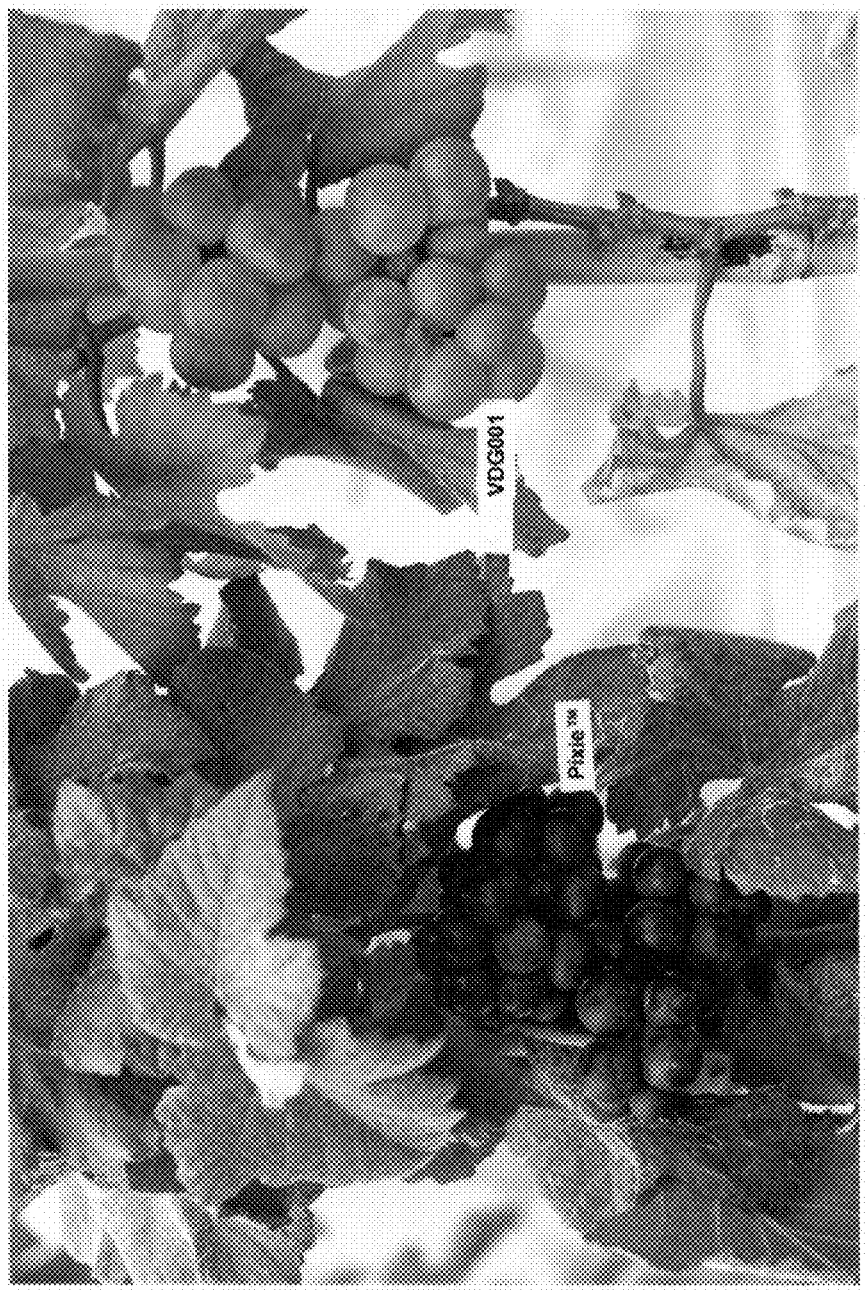
FIG. 5 shows grape bunch size and density and berry color, size and shape of 'VDG001', in comparison to the female parent 'Pixie'™.

'VDG001' is a dwarf ornamental grapevine with edible fruit. 'VDG001' has inherited the undetermined growth pattern and the dwarf growth habit from the mother variety ('Pixie'™). The internodes are 10-15 mm in length (approximately 10-20 times shorter compared to standard *Vitis vinifera* cultivars). Genotypic lab analysis confirmed the hybrid status of 'VDG001'. Polymerase chain reaction (PCR) was performed on template DNA extracted from 'VDG001' using microsatellite marker primers that were polymorphic between 'Pixie'™ and 'Riesling'. The microsatellite markers confirmed that the new variety 'VDG001' is a hybrid of the parents.

The variety is uniform and stable. No off-types, variants or mutations have been found to date.

The R.H.S. Colour Chart of The Royal Horticultural Society has been used for colour identification of foliage, berry skin and shoot. The description is based on the observation of 10 one year old plants growing in containers on their own roots in a greenhouse facility at Vineland Research and Innovation Centre, Vineland Station, Ontario, Canada during the years 2013 and 2015.

Time of bud burst: Not available as the plants were grown in a greenhouse.

Young shoot:
- *Openness of tip.*—Closed.
- *Prostrate hairs on tip.*—Dense.
- *Anthocyanin coloration on prostrate hairs on tip.*—Medium.

Young leaf:
- *Color of upper side of blade.*—Green (137-C).
- *Prostrate hairs between main veins on lower side of blade.*—Medium to sparse.

Shoot:
- *Color of dorsal side of internodes.*—Green (139-B).
- *Color of ventral side of internodes.*—Green (139-B).
- *Color of dorsal side of nodes.*—Green (139-B).
- *Color of ventral side of nodes.*—Green (139-B).
- *Length of tendril.*—Very short (abort at length of 4-5 mm).

Flower:
- *Sexual organs.*—Fully developed stamens and fully developed gynoecium.

Inflorescence:
- *Type.*—Hermaphrodite.
- *Date of bloom.*—Continuous.
- *Flower cap.*—5 fused, yellow green (146-B).
- *Flowers/cluster.*—10-80.
- *Flower diameter.*—2.2 mm.
- *Cluster length+peduncle.*—2-3 cm.
- *Pistil length.*—2.4 mm.
- *Pistil color.*—Yellow green (146-B).
- *Filament length.*—2 mm.

Mature leaf:
- *Size of blade.*—Small to very small.
- *Shape of blade.*—Circular.
- *Blistering of upper side of blade.*—Weak.
- *Number of lobes.*—Three.
- *Depth of upper lateral sinuses.*—Medium to shallow.
- *Arrangement of lobes of upper lateral sinuses.*—Closed.
- *Arrangement of lobes of petiole sinus.*—Slightly overlapped.
- *Length of teeth.*—Medium to short.
- *Ratio length/width of teeth.*—Medium.
- *Shape of teeth.*—Mixture of both sides straight and both sides convex.
- *Proportion of main veins on upper side with anthocyanin coloration.*—Absent or very low.
- *Prostrate hairs between main veins on lower side of blade.*—Sparse.
- *Erect hairs on main veins on lower side of blade.*—Medium.
- *Length of petiole compared to length of middle vein.*—Much shorter.
- *Color of upper surface.*—Yellow green (147-A).

Time of beginning of berry ripening: Not available as the plants were grown in a greenhouse.

Bunch:
- *Size (peduncle excluded).*—Very small.
- *Density.*—Dense.
- *Length of peduncle of primary bunch.*—Short.

Berry:
- *Size.*—Small.
- *Shape.*—Globose.
- *Color of skin (without bloom).*—Green (144-B, Also the berry is slightly russet).
- *Ease of detachment from pedicel.*—Difficult.
- *Thickness of skin.*—Medium.
- *Anthocyanin coloration of flesh.*—Absent or very weak.
- *Firmness of flesh.*—Soft or slightly firm.
- *Particular flavor.*—None.
- *Formation of seeds.*—Complete.

Woody shoot:
- *Main color.*—Orange brown (175-C).

Other: The petiole of 'VDG001' has some anthocyanin pigmentation, while the one in 'Pixie'™ is green. 'VDG-001' has no particular resistance to any disease or insects and its susceptibility to disease and insects is similar to that of the female parent "Pixie"™.

Biometric data of 'VDG001' is compared to that of the mother variety ('Pixie'™) in Table 1.

TABLE 1

| Biometric data | 'VDG001' | 'Pixie' ™ |
|---|---|---|
| Average size of mature leaf blade, L × W, mm | 94 × 93 | 106 × 107 |
| Length of petiole/length of main vein, mm | 36/64 | 42/77 |
| Height of central stem, cm | 108 | 98 |
| Total linear growth per plant, cm | 108 | 150 |
| Total number of nodes per plant | 82 | 117 |
| Average internode size, mm | 13 | 13 |
| First bunch set at node number | 39 | 25 |
| Average peduncle length, mm | 26.7 | 40.5 |
| Average number of berries per bunch | 10.0 | 21.6 |
| Average bunch weight, g | 16.5 | 18.9 |
| Average berry weight, g | 1.7 | 0.9 |
| Average berry size, mm | 13.7 | 12.7 |
| Average number of seeds/berry | 3.0 | 2.7 |
| Sugar content, °Bx | 20.2 | 21.3 |

The 'VDG001' variety has not been observed under all possible environmental conditions to date. Accordingly, it is possible that the phenotypic expression may vary somewhat with changes in light intensity and duration, cultural practices, and other environmental conditions.

What is claimed:

1. A new and distinct variety of dwarf ornamental grapevine substantially as herein illustrated and described.

* * * * *